(12) United States Patent
O'Keefe et al.

(10) Patent No.: US 9,140,614 B2
(45) Date of Patent: Sep. 22, 2015

(54) CONDUCTIVE CLOTH SENSOR

(71) Applicants: Patrick O'Keefe, Wellington, OH (US);
Paul Lecat, Tallmadge, OH (US)

(72) Inventors: Patrick O'Keefe, Wellington, OH (US);
Paul Lecat, Tallmadge, OH (US)

(73) Assignee: Paul Lecat, Tallmadge, OH (US)

( * ) Notice: Subject to any disclaimer, the term of this patent is extended or adjusted under 35 U.S.C. 154(b) by 88 days.

(21) Appl. No.: 14/077,255

(22) Filed: Nov. 12, 2013

(65) Prior Publication Data

US 2014/0130610 A1    May 15, 2014

Related U.S. Application Data

(60) Provisional application No. 61/725,275, filed on Nov. 12, 2012.

(51) Int. Cl.
*G01L 1/16* (2006.01)
*G01L 5/22* (2006.01)

(52) U.S. Cl.
CPC . *G01L 1/16* (2013.01); *G01L 5/228* (2013.01); *H01H 2203/01* (2013.01)

(58) Field of Classification Search
CPC .............. G01L 1/20; G01L 1/16; G01L 1/205; G01L 5/228; H01H 2203/01
USPC ......................... 73/862.381, 862.391, 862.68
See application file for complete search history.

(56) References Cited

U.S. PATENT DOCUMENTS

| 4,555,954 | A | | 12/1985 | Kim |
| 4,644,801 | A | * | 2/1987 | Kustanovich ............ 73/862.046 |
| 4,878,057 | A | * | 10/1989 | Kompanek et al. ............. 341/34 |
| 5,014,224 | A | | 5/1991 | Hans |
| 5,028,546 | A | * | 7/1991 | Hotchkiss ....................... 438/63 |
| 5,060,527 | A | * | 10/1991 | Burgess ..................... 73/862.68 |
| 6,216,545 | B1 | | 4/2001 | Taylor |
| 7,641,618 | B2 | * | 1/2010 | Noda et al. .................... 600/535 |
| 7,770,473 | B2 | | 8/2010 | Von Lilienfeld-Toal |
| 2002/0130324 | A1 | * | 9/2002 | Song et al. ....................... 257/72 |
| 2005/0048455 | A1 | | 3/2005 | Hayamitzu et al. |

(Continued)

FOREIGN PATENT DOCUMENTS

WO    WO 00/26627    5/2000

OTHER PUBLICATIONS

Korean Intellectual Property Office, International Search Report and Written Opinion; Feb. 14, 2014; (10 pages); Daejeon, South Korea.

*Primary Examiner* — Max Noori
(74) *Attorney, Agent, or Firm* — Roger D. Emerson; Emerson Thomson Bennett, LLC (57) ABSTRACT

A force sensor is disclosed herein. The force sensor includes first and second layers formed from electrically conductive material. The force sensor also includes a third layer formed from an electrically insulative material disposed between the first and second layers. The third layer is a mesh defining a distribution of plurality of spaced openings. It is also disclosed herein that the force sensor can be incorporated in an auscultation training system. The auscultation training system can also include an auscultation device operable to be pressed against the force sensor whereby the force sensor emits a signal in response to being pressed. The auscultation training system can also include a controller communicating with the force sensor and operable to receive the signal. The auscultation training system can also include a database of sound files wherein the controller is operable to select one of the sound files in response to the signal.

13 Claims, 5 Drawing Sheets

(56) References Cited

U.S. PATENT DOCUMENTS

2008/0296776 A1* 12/2008 Skog et al. .................. 257/773
2009/0218925 A1* 9/2009 Kwak .......................... 313/243
2012/0327028 A1* 12/2012 Chang et al. ................. 345/174

* cited by examiner

CONDUCTIVE CLOTH SENSOR

CROSS-REFERENCE TO RELATED APPLICATIONS

This application claims the benefit of U.S. Provisional Patent Application Ser. No. 61/725,275 for a CONDUCTIVE CLOTH SENSOR, filed on Nov. 12, 2012, which is hereby incorporated by reference in its entirety.

BACKGROUND OF THE INVENTION

1. Field of the Invention

The invention relates to force sensors formed from flexible materials.

2. Description of Related Prior Art

U.S. Pat. No. 7,770,473 discloses a pressure sensor. The pressure sensor can be incorporated into textile products. The pressure sensor includes a multilayer thread having a pressure sensitive layer exhibiting a pressure-dependent electrical resistance, and a conductive layer in contact with the pressure sensitive layer. Further, the sensor includes conductive threads in contact with the multilayer thread.

SUMMARY OF THE INVENTION

In summary, the invention is a force sensor. The force sensor includes first and second layers formed from electrically conductive material. The force sensor also includes a third layer formed from an electrically insulative material disposed between the first and second layers. The third layer is a mesh defining a distribution of plurality of spaced openings. It is also disclosed herein that the force sensor can be incorporated in an auscultation training system. The auscultation training system can also include an auscultation device operable to be pressed against the force sensor whereby the force sensor emits a signal in response to being pressed. The auscultation training system can also include a controller communicating with the force sensor and operable to receive the signal. The auscultation training system can also include a database of sound files wherein the controller is operable to select one of the sound files in response to the signal.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION OF EXEMPLARY EMBODIMENTS

A plurality of different embodiments of the invention is shown in the Figures of the application. Similar features are shown in the various embodiments of the invention. Similar features have been numbered with a common reference numeral and have been differentiated by an alphabetic suffix. Also, to enhance consistency, the structures in any particular drawing share the same alphabetic suffix even if a particular feature is shown in less than all embodiments. Similar features are structured similarly, operate similarly, and/or have the same function unless otherwise indicated by the drawings or this specification. Furthermore, particular features of one embodiment can replace corresponding features in another embodiment or can supplement other embodiments unless otherwise indicated by the drawings or this specification.

The invention, as demonstrated by the exemplary embodiment described below, provides an enhanced pressure sense. The exemplary embodiment takes the form of a cloth, a structure capable of taking the form of the surface upon which it is supported, such as a planar form when supported by a planar surface or a non-planar form when supported by a non-planar surface. Embodiments can be more rigid than a piece of single-layer fabric, but are generally pliable and elastically deformable.

Figure 2:
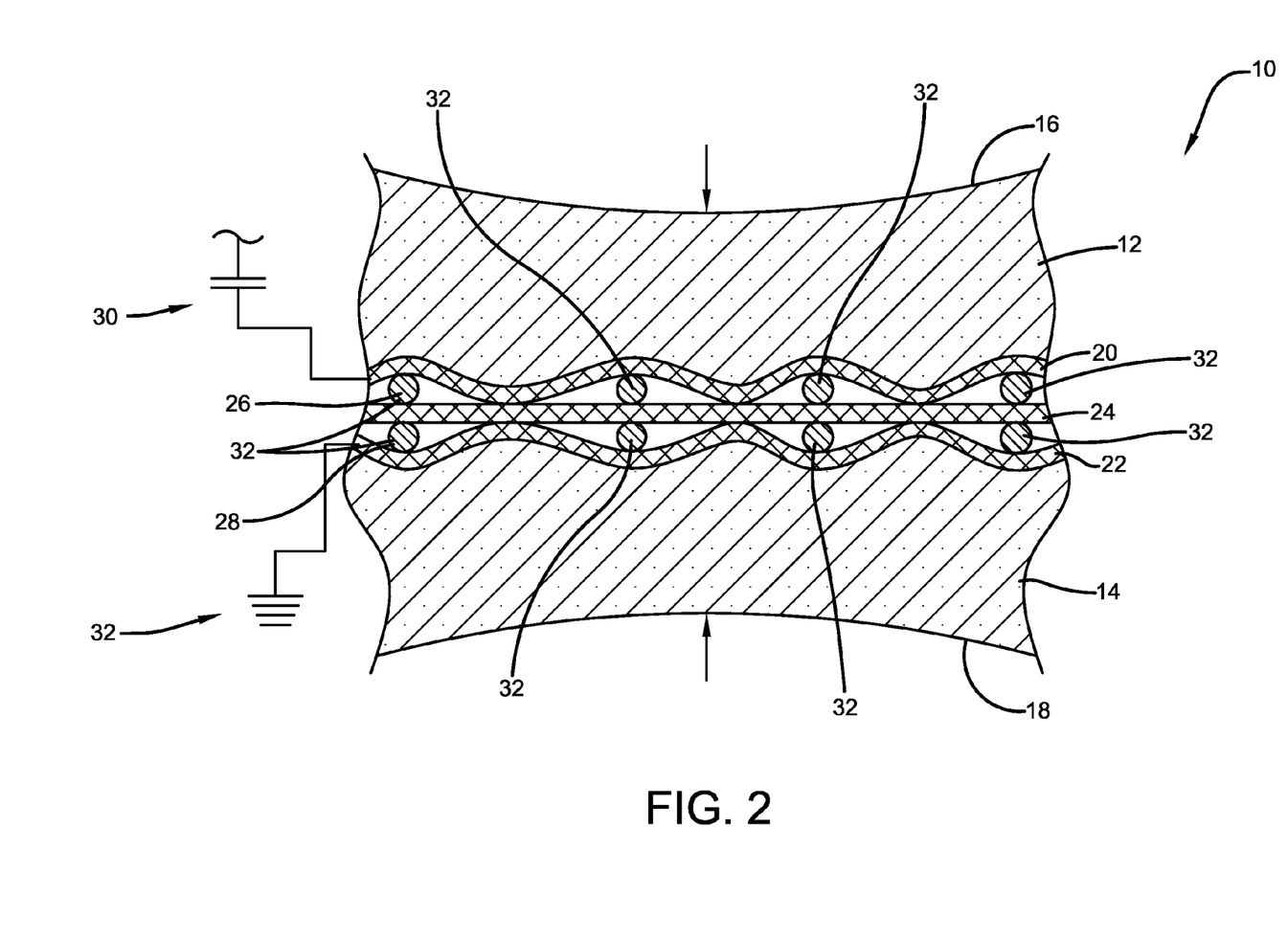
FIG. 2 is a cross-sectional view of a portion of a first exemplary embodiment of the invention being compressed.

In a first exemplary embodiment of the invention, a force sensor 10 can be formed from a plurality of pliable layers. FIG. 2 show outermost layers 12, 14 of an exemplary force sensor 10 being Neoprene foam. The foam can be closed-cell or open-cell. It can be desirable that at least one of the outer surfaces 16, 18 of one of the outermost layers 12, 14 be closed, in other words forming a skin and not open cells.

Inward of the outermost layers 12, 14 are respective layers 20, 22 of conductive fabric. In one embodiment of the invention, the conductive fabric layers 20, 22 can be pure copper polyester Taffeta fabric. The outermost layers 12, 14 and conductive fabric layers 20 can be engaged together in various ways, such as with adhesive or stitching.

Figure 1:
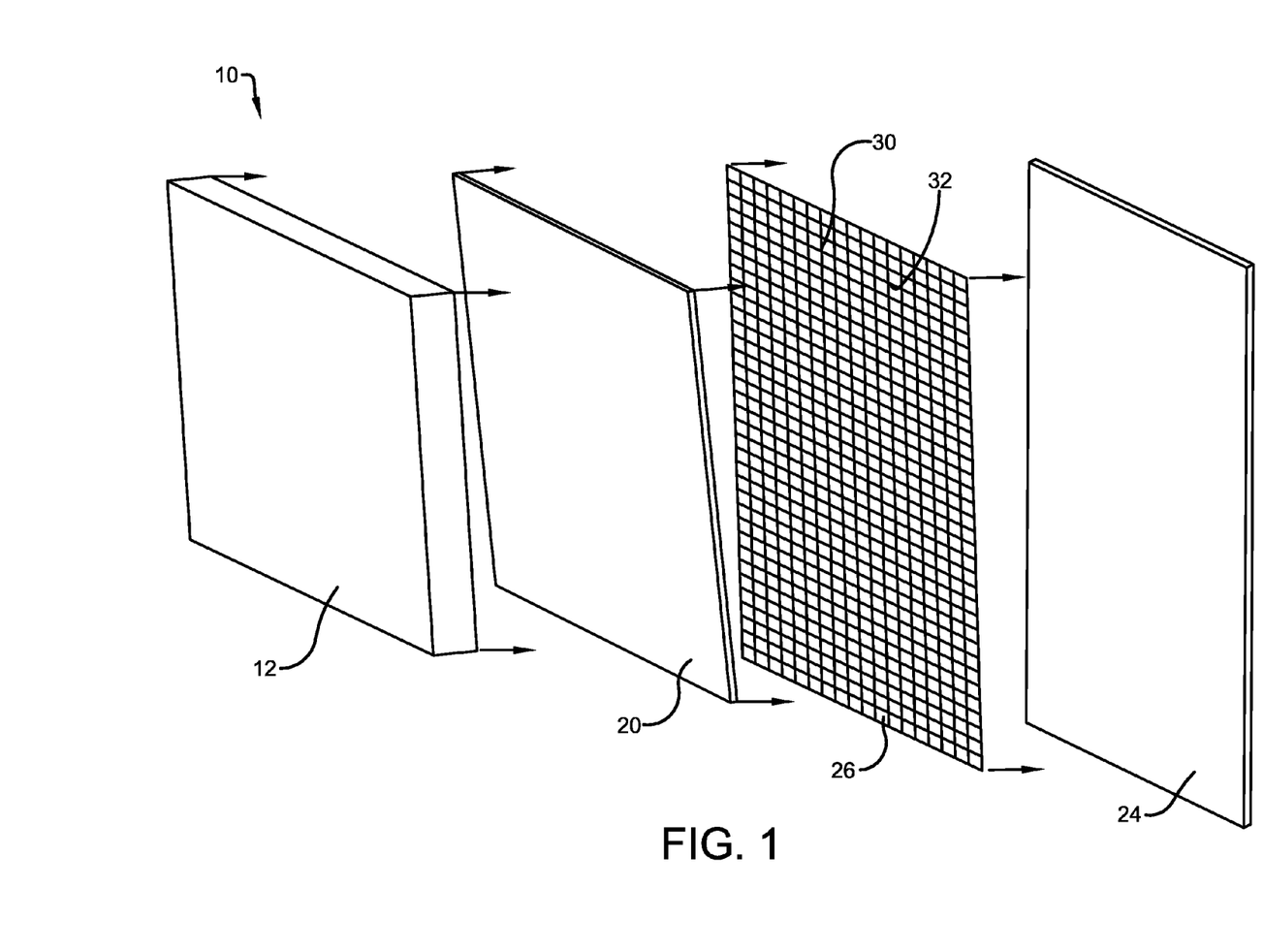
FIG. 1 is an exploded view of a central layer of an exemplary embodiment of the invention and the layers on one side of the central layer.

In the exemplary embodiment of the invention, a central layer 24 can be formed from Velostat® antistatic resistive material. This material displays the property of electric resistance. As the compressive force on the sensor 10 increases, electrical resistance through the sensor 10 decreases. For example, as increasing pressure is applied to the layers, the conductive layers press harder on the Velostat®, increasing the area of the two copper layers that is touching the Velostat®, thereby reducing the electrical resistance Layers 26 and 28 of Tulle can be positioned on opposite sides of the central layer 24 of Velostat® antistatic resistive material. Tulle is lightweight netting and is thus a mesh defining a distribution of spaced openings. The mesh of the layers 26 and 28 include warp and weft fibers or filaments, such as longitudinally-extending warp fiber 30 and transverse-extending weft fiber 32 as shown in FIG. 1. An opening in a mesh is created when adjacent warp and weft fibers are spaced from one another. For example warp or weft fibers can be spaced a distance greater than the width of one of the fibers. Conversely, in a fabric, adjacent warp and weft fibers are positioned proximate or close to one another, such as in contact with one another. The layers 26, 28 of Tulle separate the layer 24 of Velostat® antistatic resistive material from the opposing layers 20, 22 of conductive fabric. The layers 26, 28 of Tulle are formed from an insulative material.

In the operation of the exemplary embodiment of the invention, a differential electric potential can be defined between the layers 20, 22 of conductive fabric. FIG. 2 schematically shows a source of electric potential referenced at 30 and a ground connection referenced at 32. The layers of Tulle prevent the formation of a circuit between the conductive layers 20, 22 and the central layer 24 of Velostat® antistatic resistive material. When pressure is applied to the sensor 10, one or both of the layers 12, 14 of Neoprene can urge the conductive layers 20, 22 into contact with the layer 24 of Velostat® antistatic resistive material through the openings defined in the Tulle mesh layers 26, 28. FIG. 2 shows the layers 20, 22 projecting between adjacent weft fibers 32. The warp fibers 30 are not visible in FIG. 2, but the layers 20, 22 are also projecting between adjacent warp fibers 30 in the exemplary embodiment.

A circuit is thus formed and the resistance encountered by current in the circuit diminishes as the force or pressing on the sensor increases. One or both of the layers 20, 22 can be arranged with conducting fibers in a grid and sensors can be associated with one or more of the fibers so that the location of the application of pressure on the force sensor 10 can be detected.

The sensor 10 can be used as part of an auscultation training system. Auscultation is the act of listening to sounds within the body as a method of diagnosis. A stethoscope is an example of an auscultation device that is used in the medical field to listen to internal sounds in the human body, such as for example heart sounds, breathing (breath sounds), intestinal noises, and blood flow in arteries and veins. Acoustic stethoscopes operate on the transmission of sound from a headpiece, via air-filled hollow tubes, to a listener's ears. The headpiece may include a diaphragm that can be placed against a human body for sensing sound. Body sounds vibrate the diaphragm, creating acoustic pressure waves that travel through the tubing to the listener's ears.

Figure 3:
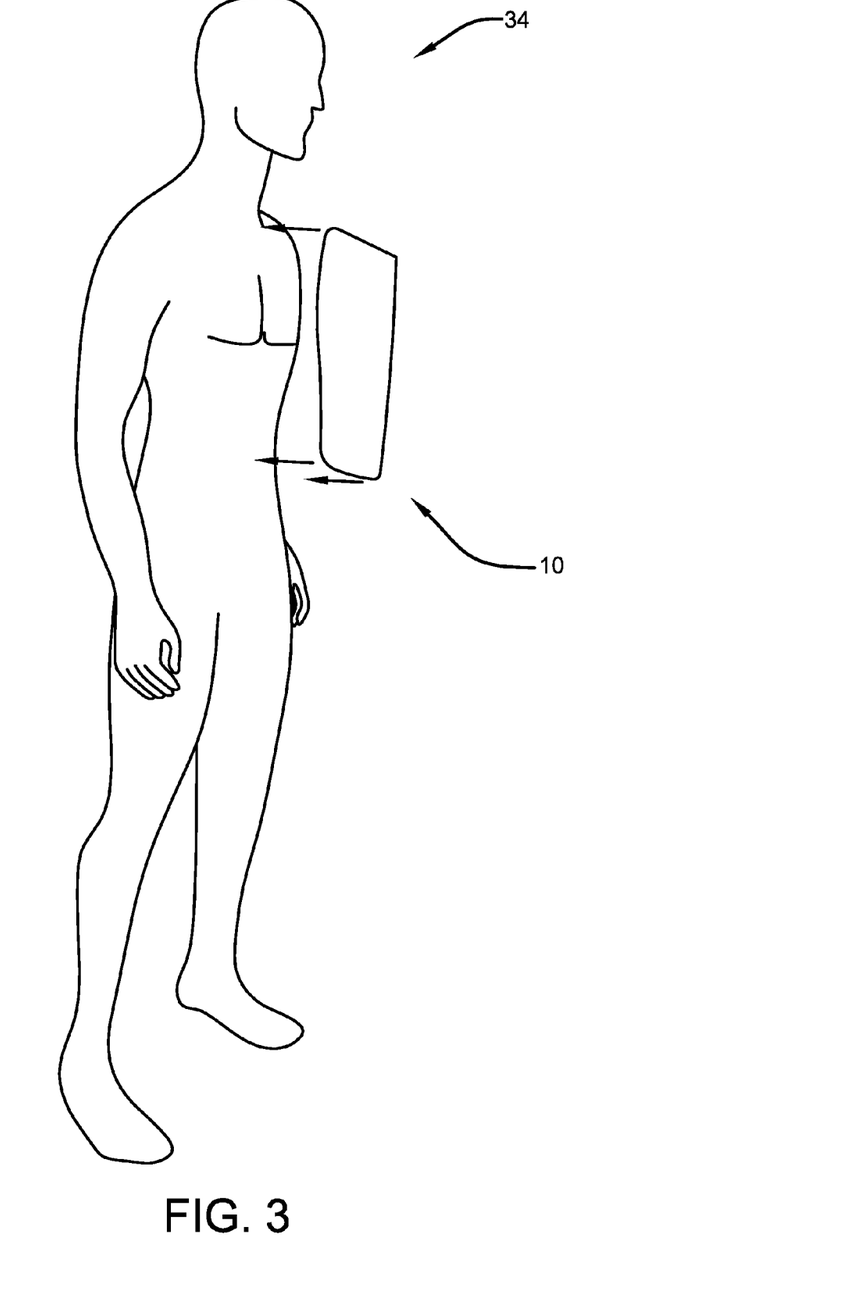
FIG. 3 is a perspective view of exemplary embodiment of the invention being positioned on an auscultation manikin.

As shown in FIG. 3, the sensor 10 can be positioned on a training manikin 34. The sensor 10 can be used to detect when a health care trainee presses a stethoscope bell on the manikin 34. Embodiments of the invention can detect the relative position of an auscultation device in relation to the manikin and relay its relative position to a controller device. The controller device is adapted to select sound data from the database that corresponds to the detected location and retrieve, or cause the retrieval of, the sound data from the database. According to some embodiments, the controller also communicates the sound data to a transmitter, or causes the sound data to be so communicated. The sound data can then be communicated by the transmitter to at least one receiver that is disposed on or in the at least one auscultation device, such as a stethoscope. The receiver can also be in electronic communication with a sound-generating device adapted to convert electronic signals from the receiver into acoustic wave signals. Such acoustic wave signals can then be audibly communicated to an ear piece and to a human ear. U.S. Pat. Nos. 7,645,141 and 8,257,089 are hereby incorporated by reference in their entireties.

Figure 4:
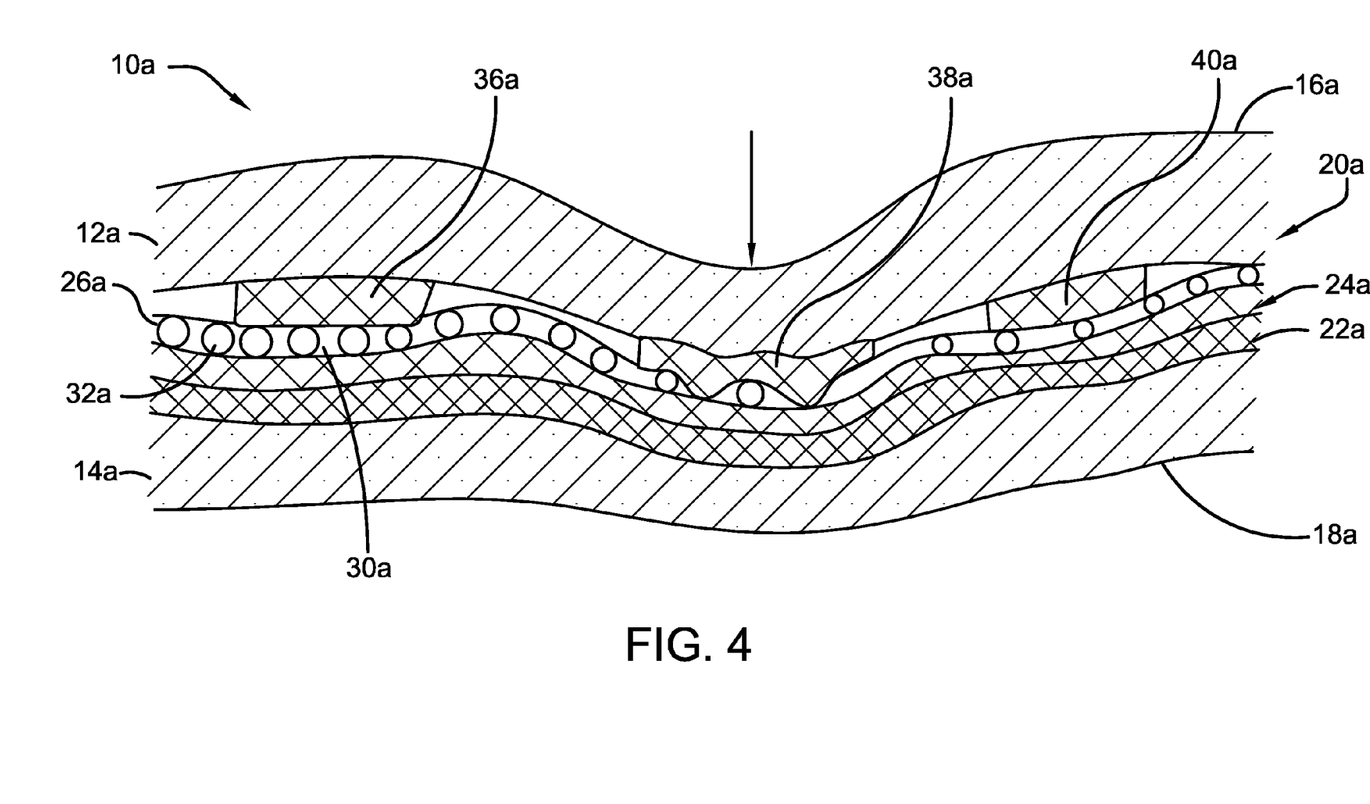
FIG. 4 is a cross-sectional view of a portion of a second exemplary embodiment of the invention being compressed.

FIG. 4 is a cross-sectional view of a portion of a second exemplary embodiment of the invention being compressed. A force sensor 10a can be formed from a plurality of pliable layers. FIG. 4 show outermost layers 12a, 14a of the exemplary force sensor 10a being Neoprene foam. The foam can be closed-cell or open-cell. It can be desirable that at least one of the outer surfaces 16a, 18a of one of the outermost layers 12a, 14a be closed, in other words forming a skin and not open cells.

Inward of the outermost layers 12a, 14a are respective layers 20a, 22a of conductive fabric. In one embodiment of the invention, the conductive fabric layers 20a, 22a can be pure copper polyester Taffeta fabric. The outermost layers 12a, 14a and conductive fabric layers 20a can be engaged together in various ways, such as with adhesive or stitching.

The exemplary layer 20a is discontinuous and the exemplary layer 22a is continuous. In FIG. 4, the layer 20a is shown including three discrete portions or islands 36a, 38a, 40a. An individual wire extends from each portion of the layer 20a to complete an individual circuit. One or more specific embodiments of the broader invention can include a layer 22a having any desired number or portions or islands.

In the exemplary embodiment of the invention, a central layer 24a can be formed from Velostat® antistatic resistive material. This material displays the property of electric resistance. As the compressive force on the sensor 10a increases, electrical resistance through the sensor 10a decreases. For example, as increasing pressure is applied to the layers, the conductive layers press harder on the Velostat®, increasing the area of the two copper layers that is touching the Velostat®, thereby reducing the electrical resistance Layer 26a of Tulle can be positioned between the central layer 24a of Velostat® antistatic resistive material and the layer 20a. Tulle is lightweight netting and is thus a mesh defining a distribution of spaced openings. The mesh of the layer 26a includes warp and weft fibers or filaments, such as longitudinally-extending warp fiber 30a and transverse-extending weft fiber 32a. An opening in the mesh is created when adjacent warp and weft fibers are spaced from one another. For example warp or weft fibers can be spaced a distance greater than the width of one of the fibers. Conversely, in a fabric, adjacent warp and weft fibers are positioned proximate or close to one another, such as in contact with one another. The layer 26a of Tulle is formed from an insulative material.

In the operation of the exemplary embodiment of the invention, a differential electric potential can be defined between the layers 20a, 22a of conductive fabric. The layer 26a of Tulle prevents the formation of a closed circuit between the conductive layers 20a, 22a and the central layer 24a of Velostat® antistatic resistive material. When pressure is applied to the sensor 10a, one or both of the layers 12a, 14a of Neoprene can urge the conductive layers 20a, 22a into contact with the layer 24a of Velostat® antistatic resistive material through the openings defined in the Tulle mesh layer 26a. FIG. 4 shows the portion 38a of the layer 20a projecting between adjacent weft fibers 32a. Multiple warp fibers 30a are not visible in FIG. 4, but the layer 20a also projects between adjacent warp fibers 30a in the exemplary embodiment.

A circuit is thus formed and the resistance encountered by current in the circuit diminishes as the force or pressing on the sensor increases. One or both of the layers 20a, 22a can be arranged with conducting fibers in a grid and sensors can be associated with one or more of the fibers so that the location of the application of pressure on the force sensor 10a can be detected.

Figure 5:
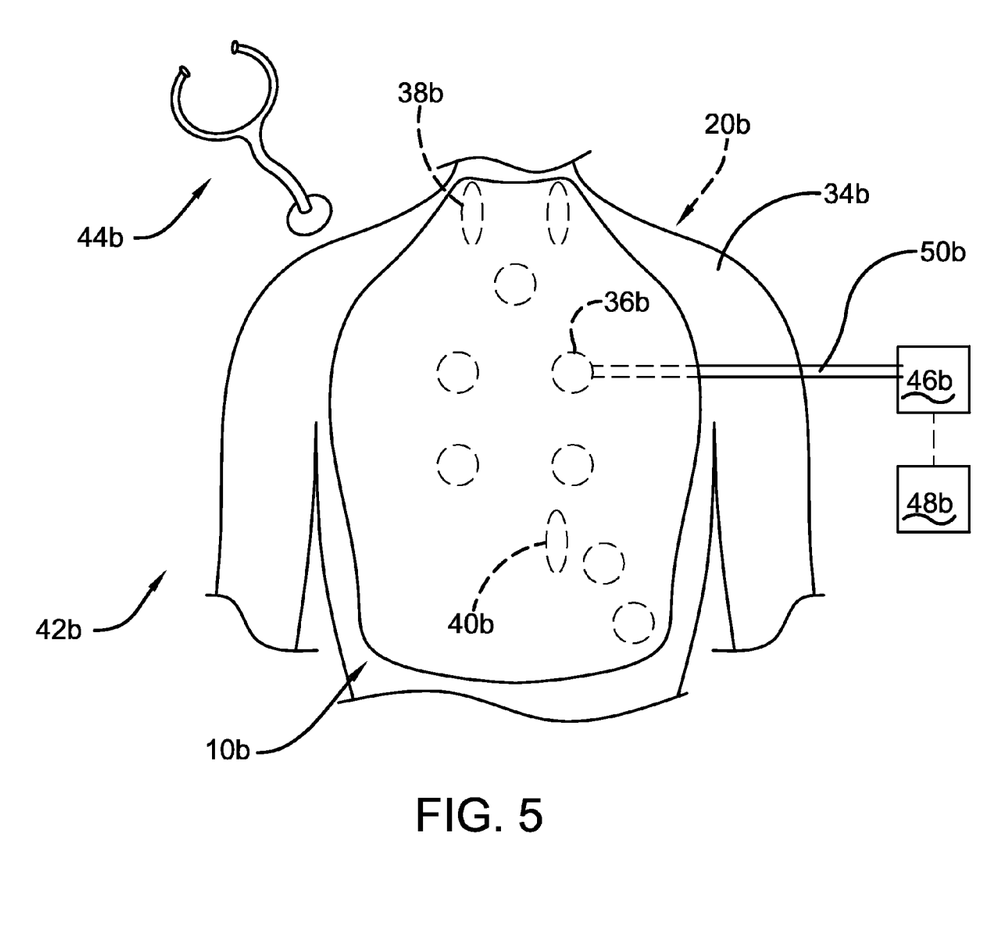
FIG. 5 is a top-down view of a third exemplary embodiment of the invention laid upon a manikin.

FIG. 5 is a top-down view of a third exemplary embodiment of the invention laid upon a manikin 34b. The sensor sheet 10b includes a plurality of individual sensors mounted together in a multi-layer structure. The sensor sheet 10b can have the same structure as shown in FIG. 4. A conductive layer 20b is discontinuous and includes a plurality of discrete portions spaced from one another, such as portion 36b. The portions of layer 20b are shown in dash line since the portions are embedded in the sensor sheet 10b and not visible. The exemplary layer 20b includes portions of different sizes, as shown by a comparison of portions 38b and 40b. The exemplary layer 20b includes portions of different shapes, as shown by a comparison of portions 36b and 38b. The portions of the layer 20b are arranged in an irregular pattern—a pattern that is not a true, x-y grid.

FIG. 5 also shows that one or more embodiments can be part of an auscultation training system 42b. The system 42b includes the sensor sheet 10b, an auscultation device in the form of a stethoscope 44b, a controller/cpu 46b, and a database 48b of sound files. In operation, the auscultation device 44b can be worn by a trainee. The trainee can press the auscultation device 44b against the sensor sheet 10b to replicate the examination of a real patient. When an area of the sensor sheet 10b having a portion of the layer 20b is pressed, such as portion 36b, the compression of the layers will complete a circuit. A signal (such as a level of voltage or current) will be emitted through the circuit including the portion 36b. The controller 46b communicates with the circuit including the portion 36b, such as wirelessly or through a wire 50b, and is operable to receive the signal. In response to receiving the signal, the controller 46b is operable to select one of the sound files stored in the database. The controller 46 can also transmit the sound file wirelessly or otherwise to the auscultation device 44b and the sound will be emitted in the ear pieces of the auscultation device 44b.

Each of the foregoing components can be in communication with one or more of the other components by any appropriate means including wireless and hardwired electronic connections. Furthermore, each component can be physically disposed in an on-board relation to any other component or can be in a remote physical relation to any other component. For example, in some embodiments all of the foregoing components are contained in a single physical unit. In other embodiments each of the foregoing components is remote relative to each of the other foregoing components. Still other embodiments are somewhere between these extremes, wherein some components are grouped together into physical units and others are remote from each other. A wide variety of relations can be appropriate depending on the specific application, and one of skill in the art will be able to select a desired relation without undue experimentation.

Any of a wide variety of wireless communications means can be appropriate for data and/or control signal transmission. For instance, some appropriate means can include radio or infrared communications means. More specifically, some appropriate protocols include, without limitation WiFi, Bluetooth® (Bluetooth is a registered certification mark of Bluetooth Sig Inc., Bellevue, Wash.), ZigBee® (ZigBee is a registered trademark of ZigBee Alliance Corp., San Ramon, Calif.) and the like. Similarly, any of a wide range of hardwired connections can be appropriate. Some such connections include, without limitation, serial bus, parallel bus, SCSI, I2C (inter-integrated circuit), SPI (serial peripheral interface), and the like or any combination thereof. One of skill in the art will recognize that a wide range of wireless and hardwire technologies are available, and will be able to select an appropriate technology without undue experimentation.

Embodiments of the invention can be capable of determining the region of the manikin to which a trainee is applying the auscultation device. For example, some embodiments can localize the auscultation device in a heart region, a lung region, any of a variety of visceral or thoracic regions, and the like. Alternatively, other embodiments are adapted to triangulate the position of the auscultation device. According to such embodiments, the auscultation device is fitted with a transmitter beacon for broadcasting a predetermined signal. The manikin includes two or more receivers adapted to receive the transmitter's beacon signal, and data obtained from the receivers can be analyzed according to known algorithms to calculate the position of the auscultation device relative to the manikin. The present invention is not limited to the use of triangulation or proximity switches. Alternative devices can be used to determine the relative position of an auscultation device, and one of skill in the art will be able to select an appropriate device without undue experimentation.

In some embodiments the controller can be in hardwired electronic communication with the means for detecting the relative position of an auscultation device. For example, in some embodiments the controller can be disposed on or in the manikin and may be linked to the means for detecting relative position by at least one hardwired electrical connection. In other embodiments, the controller may be hardwired, but also disposed apart from the manikin, for example, in a desktop or handheld module. In still other embodiments, the controller can be in wireless communication with the means for detecting relative position.

Some embodiments also include a database. Suitable databases can comprise any appropriate data structure such as, without limitation, lists, hash tables, or hierarchical, relational, or network models. In some embodiments the database simply comprises a group of sound files stored together on, for instance, a CD-ROM or flash memory. The database can be stored on any appropriate machine memory means including, without limitations, volatile or nonvolatile memories, EPROMs, EEPROMs, magnetic media such as tapes or hard drives, optical media such as CD-ROMs, and the like or any combination thereof. Furthermore, the database can be physically disposed in any of a variety of locations. For example, in some embodiments the database may be an on-board component of the manikin. In other embodiments, the database may be a disposed apart from the manikin and may be a component of the controller unit, or a component of a module hardwired thereto. In still other embodiments the database may be physically disposed in a standalone, desktop or handheld means, or even as a component of the auscultation device.

Sounds can be selected in and retrieved from the database by one or more of a variety of means. In some embodiments a sound is automatically selected according to the detected position of the auscultation device. For instance, if the system determines that the auscultation device is positioned over the heart region of the manikin, then a heart sound is selected.

Alternatively, sound data may be selected and retrieved from the database according to a computer program. For instance, a program may select a particular sound based on several factors including the detected position of the auscultation device, the condition of the simulated patient (e.g. is the simulated patient experiencing a myocardial infarction), and the status of other simulator components (e.g. have chest compressions, defibrillation, or a simulated drug injection been detected). Additionally, some programs may include a weighted randomness factor, wherein the system selects a sound according to several factors, but also includes a degree of randomness in its selection.

Some embodiments also include a transmitter suitable for transmitting auscultation sound data. The transmitter can be physically disposed in any of a variety of locations depending upon the specific application. For instance, the transmitter may be an on-board component of the manikin, the controller, the database or any combination thereof. Accordingly, suitable transmitters can receive auscultation sound data though hardwire connections or wirelessly depending upon the specific architecture adopted. In one embodiment, the controller receives data indicating the position of an auscultation device relative to the manikin, selects and retrieves a corresponding sound file from the database and communicates the sound file through a hardwire connection to the transmitter, which then wirelessly transmits the sound file. One of skill in the art will recognize that this is only one of many possible architectures.

Some embodiments also include a receiver adapted to receive signals broadcast by the transmitter. The receiver can be disposed in any appropriate location on or in the auscultation device. For instance, in one embodiment the receiver can be disposed in the head piece of a stethoscope. The receiver can be adapted to convert a signal received from the transmitter into an electrical signal and communicate the signal to a sound generation device such as, without limitation, a speaker. Typically, the receiver is hardwired to the sound generation device; however, this is not required. In one example, the receiver and speaker are disposed in the head piece of a stethoscope. Therefore, the auscultation sound signal is converted into an acoustic wave within the head piece and audibly communicated to a listener's ears in the same way that the stethoscope normally transmits auscultation sounds.

Additionally, some embodiments can include a plurality of auscultation devices each having a receiver. For instance, it may be desirable to have a first auscultation device for a student and a second auscultation device for an instructor, so that the student and instructor can both listen to the same auscultation sound. Furthermore, it may be desirable to have an auscultation device for each of a plurality of students and for one or more instructors. Accordingly, an entire class can listen to the same auscultation sound simultaneously through their own devices. This may be especially beneficial, for instance, when an instructor is teaching a class the meaning of a particular sound.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Further, the "invention" as that term is used in this document is what is claimed in the claims of this document. The right to claim elements and/or sub-combinations that are disclosed herein as other inventions in other patent documents is hereby unconditionally reserved.

What is claimed is:

1. A resistive force sensor comprising:
   first and second layers formed from electrically conductive material;
   at least one third layer formed from an electrically insulative material disposed between said first and second layers, and
   a fourth layer formed from an electrically resistive material disposed between said first and second layers, wherein said third layer is a mesh defining a distribution of plurality of spaced openings, further wherein an applied force to the resistive force sensor causes an increase in mutual contact area between the fourth layer and the first and second layers, which in turn causes a decrease in resistance between the first and second layers.

2. The force sensor of claim 1 wherein said third layer is further defined as Tulle.

3. The force sensor of claim 1 wherein at least one of said first and second layers is discontinuous.

4. The force sensor of claim 3 wherein said first layer is discontinuous and includes a plurality of discrete portions spaced from one another.

5. The force sensor of claim 4 wherein said plurality of discrete portions include portions of different sizes.

6. The force sensor of claim 4 wherein said plurality of discrete portions include portions of different shapes.

7. The force sensor of claim 4 wherein said plurality of discrete portions include portions are arranged in an irregular pattern.

8. The force sensor of claim 1 wherein both of said first and second layers are continuous.

9. The force sensor of claim 1 further comprising: at least one fifth layer formed from an electrically insulative material and being a mesh defining a distribution of plurality of spaced openings, wherein said fourth layer is positioned between said fifth and third layers.

10. The force sensor of claim 9 wherein at least one of said third layer and said fifth layer is further defined as Tulle.

11. The force sensor of claim 1 further comprising: fourth and fifth layers being elastically deformable, said first layer and said second layer and said third layer disposed between said fourth and fifth layers.

12. An auscultation training system comprising: the force sensor according to claim 1; an auscultation device operable to be pressed against said force sensor whereby said force sensor emits a signal in response to being pressed; a controller communicating with said force sensor and operable to receive the signal; and a database of sound files wherein said controller is operable to select one of said sound files in response to said signal.

13. The auscultation training system of claim 12 further comprising: a manikin wherein said force sensor is laid on top of said manikin.

* * * * *